US010206405B2

(12) United States Patent
Kumar Singh

(10) Patent No.: US 10,206,405 B2
(45) Date of Patent: Feb. 19, 2019

(54) MYCOHERBICIDAL COMPOSITION FOR SUPPRESSING WATER HYACINTH

(71) Applicants: Praharaju Laxminarayana, Hyderabad (IN); Ajay Kumar Singh, Hyderabad (IN)

(72) Inventor: Ajay Kumar Singh, Hyderabad (IN)

(*) Notice: Subject to any disclaimer, the term of this patent is extended or adjusted under 35 U.S.C. 154(b) by 80 days.

(21) Appl. No.: 15/114,109

(22) PCT Filed: Jan. 23, 2015

(86) PCT No.: PCT/IN2015/000046
§ 371 (c)(1),
(2) Date: Jul. 26, 2016

(87) PCT Pub. No.: WO2015/111082
PCT Pub. Date: Jul. 30, 2015

(65) Prior Publication Data
US 2017/0208818 A1    Jul. 27, 2017

(30) Foreign Application Priority Data

Jan. 27, 2014  (IN) .............................. 327/CHE/2014

(51) Int. Cl.
*A01N 63/04* (2006.01)
*A01N 61/02* (2006.01)
*A01N 63/00* (2006.01)
*C12R 1/645* (2006.01)

(52) U.S. Cl.
CPC .............. *A01N 63/04* (2013.01); *C12R 1/645* (2013.01)

(58) Field of Classification Search
CPC ................................ A01N 63/04; C12R 1/645
See application file for complete search history.

(56) References Cited

U.S. PATENT DOCUMENTS 5,434,121 A     7/1995  Gohbara et al.
6,143,312 A *  11/2000  Gohbara et al. .............. 424/408

FOREIGN PATENT DOCUMENTS

EP           0839449 A1      5/1998

OTHER PUBLICATIONS

Zhang W.M. et al., "Effect of dew period and temperature on the ability of Exserohilum monoceras to cause seedling mortality of Echinochloa species", Plant Disease, Jun. 1997, vol. 81, No. 6, pp. 629-634. (Year: 1997).*
Irwin J. et al., "Pathogen Risks Associated with Bulk Maize Imports to Australia from the United States of America", A Report by Technical Working Group 1, Mar. 1999, total document pp. 1-206. (Year: 1999).*
Tosiah, S. et al., "Efficacy of Exserohilum monoceras, a Potential Fungi for Biocontrol of Echinochloa Species," J. Trop. Agric. and Fd. Sc., 2011, pp. 117-124, vol. 39, No. 1.
Morita, A. et al., "Molecular Organization of the Mating Type (Mat) Locus of Exserohilum monoceras (Setosphaeria monoceras), a Bioherbicide Agent for Echinochloa Weeds," Mycoscience, 2012, pp. 92-101, vol. 53.
Hailmi, M.S. et al., "Potential of Exerohilum monoceras as a Bioherbicide for Controlling Enchinochloa crus-galli (Rumput Sambau)," J. Agrobiotech., 2011, pp. 1-15, vol. 2.
Zhang, W.M. et al., "Characterization of Growth and Conidia Production of Exserohilum monoceras on Different Substrates," Biocontrol Science and Technology, 1997, pp. 75-86, vol. 7.
Abdel Rahim, A.M. et al., "Pathogenicity of Fungi and Bacteria from the Sudan to Water Hyacinth," Weed Research, 1984, pp. 233-238, vol. 24.
Shabana, Y.M., "The Use of Oil Emulsions for Improving the Efficacy of Alternaria eichhomiae as a Mycoherbicide for Waterhyacinth (*Eichhornia crassipes*)," Biological Control, 2005, pp. 78-89, vol. 32.
Babu, R.M. et al., "Solid Substrate for Production of Alternaria alternata Conidia: A Potential Mycoherbicide for the Control of *Eichhornia crassipes* (Water Hyacinth)," Weed Research, 2004, pp. 298-304, vol. 44.
Shabana, Y.M. et al., "Alternaria eichhomiae, A Biological Control Agent for Waterhyacinth: Mycoherbicidal Formulation and Physiological and Ultrastructural Host Responses," European Journal of Plant Pathology, 1997, pp. 99-111, vol. 103.
Praveena, R. et al., "Fungi Occurring on Water Hyacinth [Eichhornia crassipes (Mart.) Solms] in Kerala," Journal of Tropical Agriculture, 2004, pp. 21-23, vol. 42.
Ray, P. et al., "Fungi Associated with Eichhornia crassipes in South Africa and their Pathogenicity Under Controlled Conditions," African Journal of Aquatic Science, 2012, pp. 323-331, vol. 37.
Dagno, K. et al., "Synthese Bibliographique: Problematique de la jacinthe d'eau, Eichornia cassipes, dans les regions tropicales et substropicales du monde, notamment son eradication par la lutte biologique au moyen des phtopathogenes," Biotechnol. Agron. Sic. Environ., 2007, pp. 299-311.
Anonymous, "Setosphaeria monoceras," Catalogue of Life, 2014.

* cited by examiner

*Primary Examiner* — Satyendra K Singh
(74) *Attorney, Agent, or Firm* — William J. Clemens; Shumaker, Loop & Kendrick, LLP

(57) ABSTRACT

The present invention deals with a mycoherbicidal isolate of *Setosphaeria monoceras* sp. or extracts obtained therefrom, useful for the control of Water hyacinth. The present invention also discloses biological control compositions comprising fungal isolate extract formulated in a growth medium for maintaining the viability of extract when the biological control composition is applied to weed. The present invention also discloses methods of screening fungal isolate to determine if they exhibit biocontrol activity. The present invention also discloses use of *Setosphaeria monoceras* strain. In yet a further aspect the invention relates to use of an *Setosphaeria* strain for producing a herbicidal agent effective for controlling growth of water hyacinth plants. The strain used preferably is a strain having the characterizing features of *Setosphaeria* strain AGWH#1 1 as deposited at IMTECH under accession number MTCC 5974. The present invention to provide the 18s rRNA sequence analysis showed 96% nucleotide similarity of the Fungi to *Setosphaeria monoceras*. (AGBIO designated AGWH#1 1/NCIM1370/MTCC 5974) but also indicated nucleotide variation of this fungus from other known genus of *Bipolaris*, Pleosporaceae, *Cochiliobolus*, *Alternaria* including an environmentally acceptable alternative to synthetic chemical herbicides for the control of weeds, such as Water hyacinth. The present invention also discloses methods of whole genome study of strain.

5 Claims, 9 Drawing Sheets

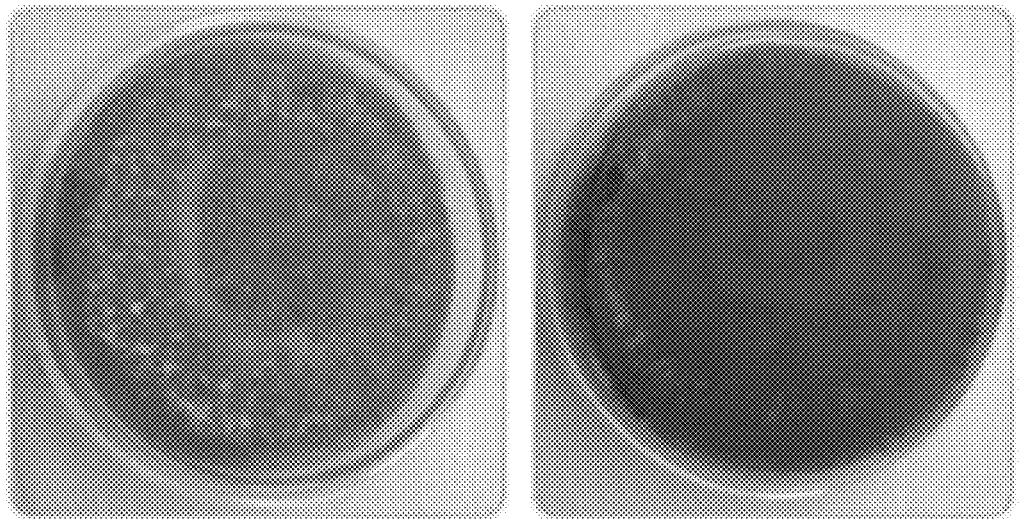
Fig 3 illustrates the macroscopic features of strain in accordance with present invention;
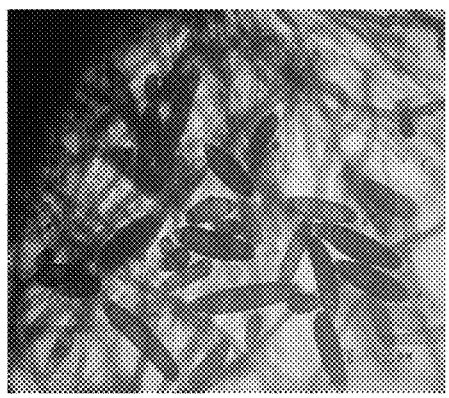
Fig 4 illustrates the microscopic features of the strain in accordance with present invention

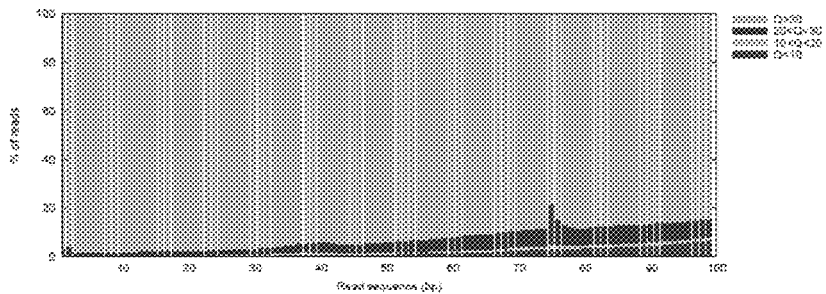

Fig 5 illustrate base quality score distribution left (R1) end of the paired end read for strain sample in accordance with present invention;

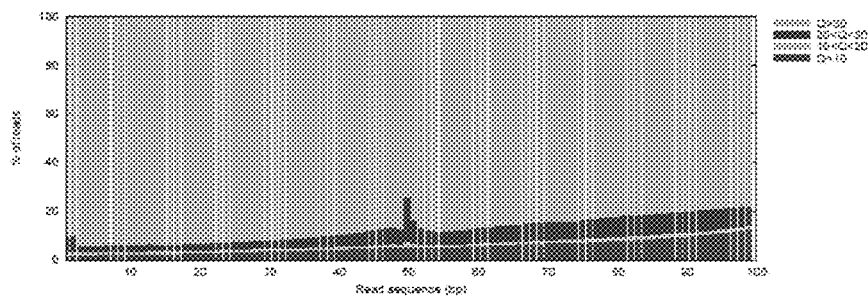

Fig 6 illustrate base quality score distribution right (R2) end of the paired end read for the strain sample in accordance with present invention

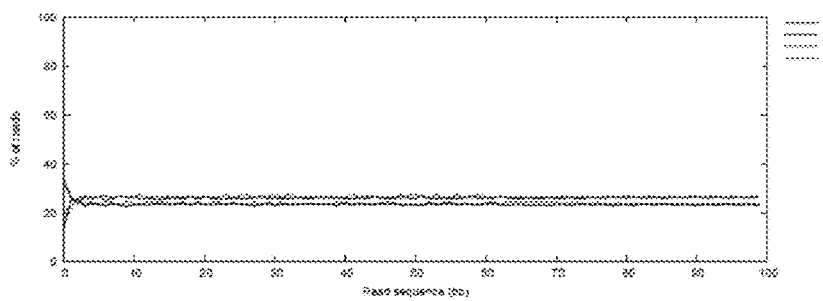

Fig 7 illustrate base composition distribution of left end of the paired end read sequence for the fungal sample in accordance with present invention;

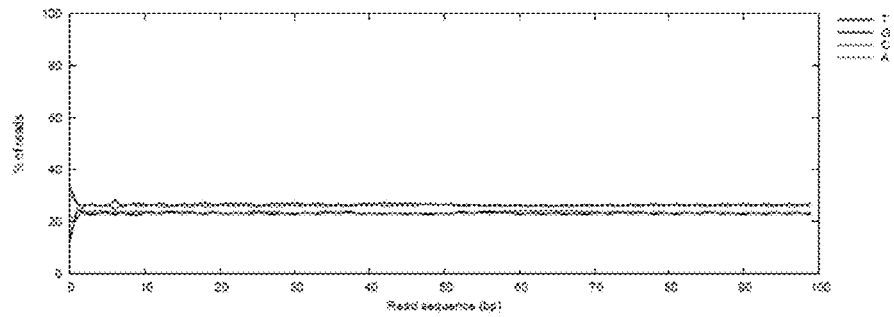
Fig 8 illustrate base composition distribution of right end of the paired end read sequence
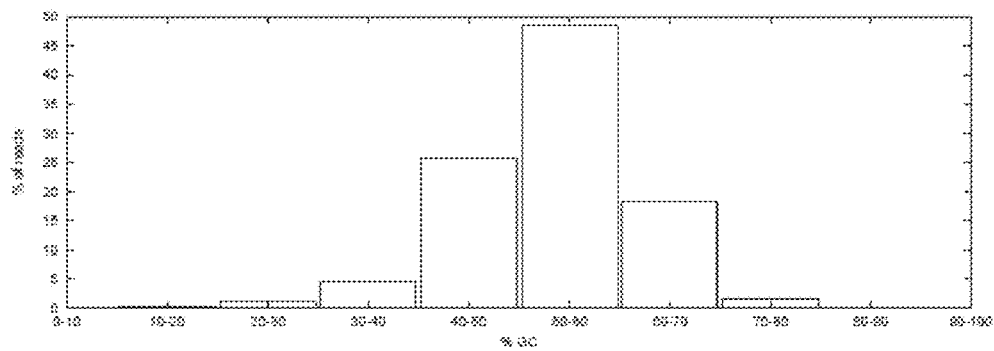
Fig 9 illustrate the GC distribution of left end of the paired end read sequence for the fungal sample in accordance with present invention;
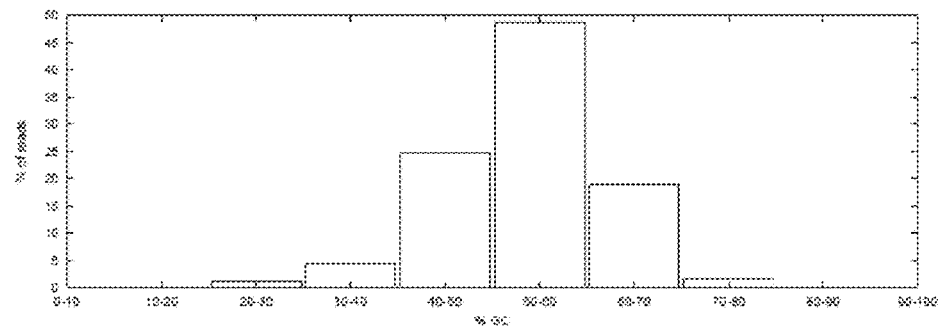
Fig 10 illustrate The GC distribution of left and right end of the paired end read sequence

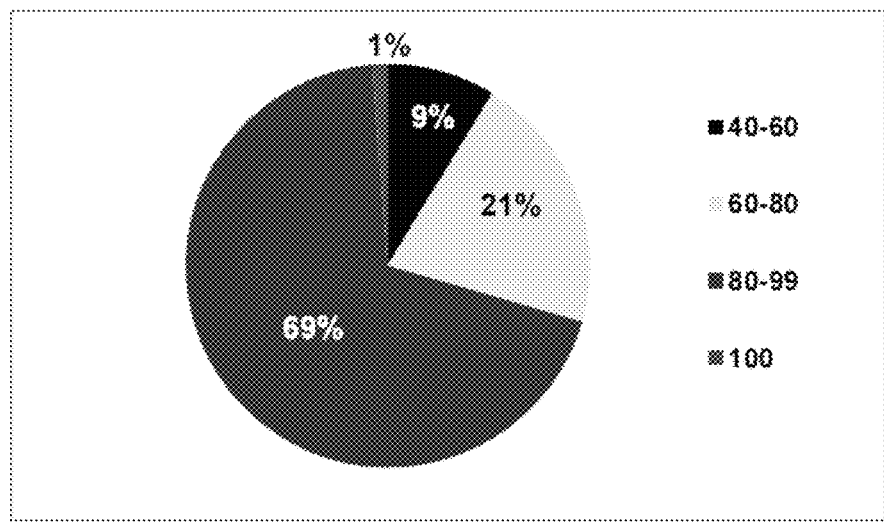
Fig 11 illustrates BLASTX E Value distribution for the fungal sample in accordance with present invention;

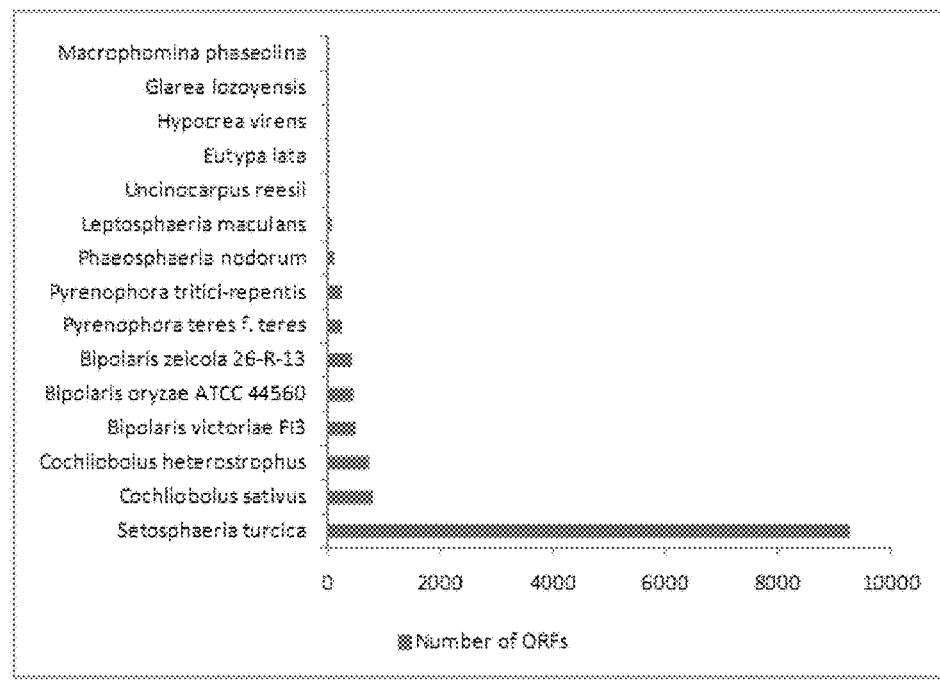
Fig 12 illustrate annotated result of top 15 organisms found in BLASTX for the fungal sample in accordance with present invention;

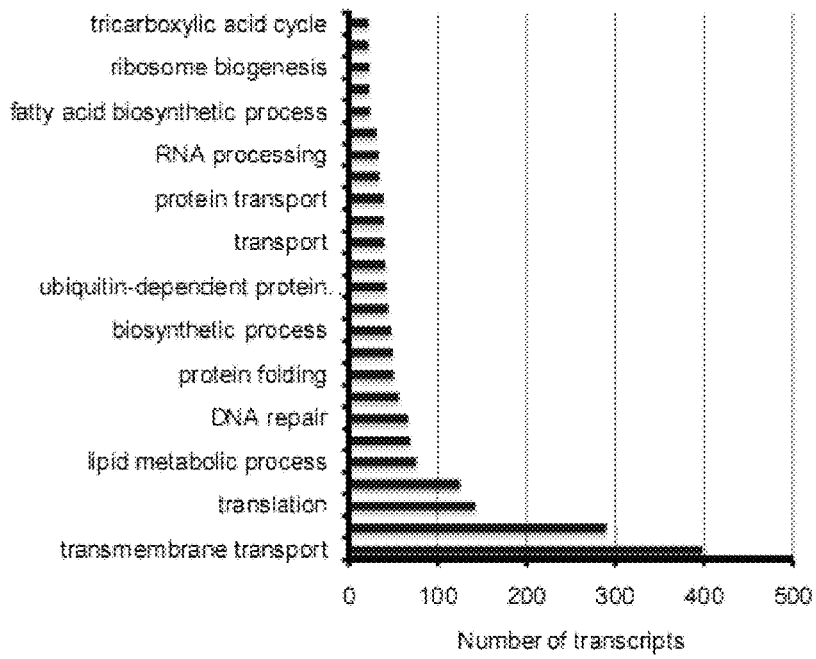
Fig 13 illustrate top 13 terms in biological function category identified using Gene ontology annotation for sample in accordance with present invention;
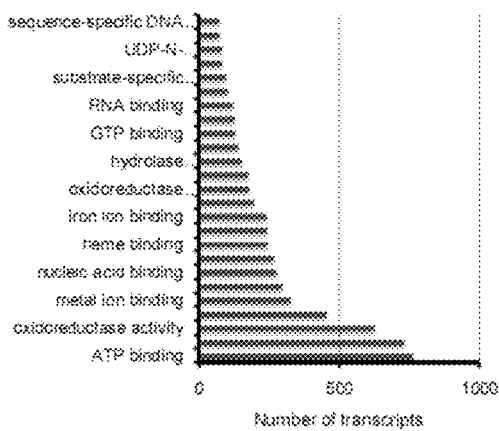
Fig 14 illustrate top 13 terms in molecular function category identified using Gene ontology annotation for sample in accordance with present invention;

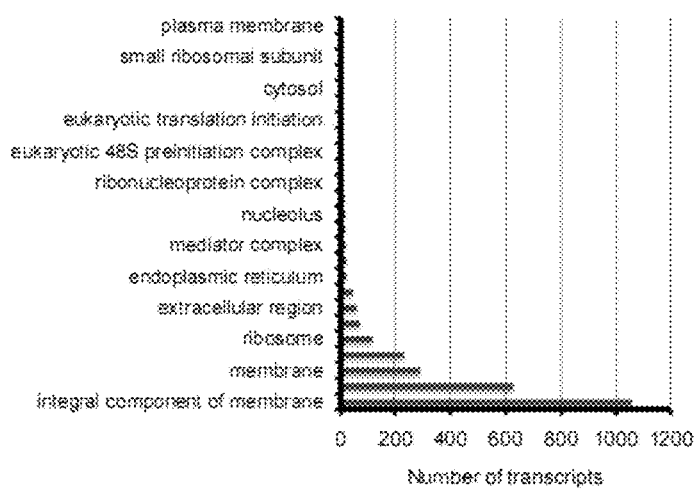
Fig 15 illustrate top 13 terms in cellular component category identified using Gene ontology annotation for sample in accordance with present invention

MYCOHERBICIDAL COMPOSITION FOR SUPPRESSING WATER HYACINTH

FIELD OF THE INVENTION

The present invention provides a novel herbicidal isolate of *Setosphaeria monoceras*. And further relates to a composition and a method for biological control of Water hyacinth. The isolate's spores, cell free culture filtrate, crude metabolites and pure purified phytotoxin obtained therefrom, useful for the control of potential biological control agent for water hyacinth. The present invention also discloses herbicidal compositions comprising fungal isolates formulated in a growth medium for maintaining the viability of the product when the biological control composition is applied to weed. The present invention also discloses methods of screening fungal isolates to determine if they exhibit biocontrol activity. The present invention also discloses a whole genome study for detecting *Setosphaeria monoceras*. isolates that exhibit biocontrol activity to water hyacinth.

BACKGROUND OF THE INVENTION

Water hyacinth (*Eichhornia* sp.) is a genus of noxious aquatic weeds. The genus includes the species *Eichhornia azurea, Eichhornia crassipes, Eichhornia diversifolia, Eichhornia paniculata*. In India, more than 200,000 ha of water surface is infected by plants from this genus. It poses serious economic, social and environmental problems in India and many countries in tropics and subtropics. It shows that the plant's reproductive capacity, adaptability, nutritional requirements and resistance to adverse environments make it impossible to eradicate, and difficult to control. The problem of the spread of water hyacinth in the waterways and banks, which causes them to waste water by increasing the rate of transpiration and great rival for fish and plankton and then change the natural qualities of water as a result of the decomposition of the plant and the consumption of dissolved oxygen and thus aquatic life. It is a free-floating aquatic macrophyte, reproducing both vegetatively via ramets formed from axillary buds on stolons, and sexually through seed production.

A variety of methods have been tried to curb the growth of the weed. Herbicides are used most often, because they provide an immediate action tool, although, they are costly and may have toxic effects if not applied according to the manufacturers' instructions. There is currently much concern about the use of synthetic chemical herbicides, such as glyphosate, to control weeds. Consequently, the use of synthetic chemical herbicides is already barred or restricted in many areas of world.

Because of the reproductive capacity and fast growth of water hyacinth, it has been necessary to use a set of biocontrol agents to increase the biotic stress in order to reduce population resurgence. Among the natural enemies of water hyacinth, plant pathogens and its metabolites can be useful because, they are often host-specific (no risk to crops, native plants or animals), easy to propagate and disseminate and self-maintaining, thus reducing the need for repeated applications. However as is the case for other biopesticides, microbial herbicides are inactivated in the environment by exposure to temperature, low humidity and ultraviolet radiation. In fact, the main problem of biopesticides is their large-scale production in a formulation that allows for a successful application in the field. Among plant pathogens, fungi are the most important natural plant pathogens. Many fungal pathogens have been cited in the literature as potential biocontrol agents for water hyacinth. Among them are *Cercosporapia ropi* (=*C. rodmanii*), *Acremonium zonatum, Alternaria eichhorniae, Myrothecium roridum, Rhizoctonia solani* and *Uredo eichhorniae*. *A. eichhorniae* and *C. piaropi*, have been studied for their biology, biocontrol potential, host specificity formulation and have been tested in experimental conditions.

However, no commercial bioherbicide for water hyacinth is available. Biological control reduces weed vigour, combined with environmental conditions, phenology of the plant and integrated use of other management options. The use of bioherbicides as biocontrol agents is therefore attracting considerable attention. Bioherbicides are typically endemic and applied inundatively to control undesired vegetation. In particular, mycoherbicides are bioherbicides based on fungal plant pathogens. The principal objective in dealing with weeds is to reduce competition from the weeds so as to allow the desired plants to grow freely. Accordingly, biocontrol of weeds addresses concerns about the effects of chemicals on environmental integrity and human health.

Objects of the Present Invention

In a first aspect, the present invention provides a herbicidal composition suitable for controlling water hyacinth, the composition comprising a herbicidal agent from an *Setosphaeria* sp, in particular strain AGWH#11. This strain is on deposit in the patent collection of the IMTECH under the terms of the Budapest Treaty and has been assigned accession number MTCC 5974. It is also deposited in NCIM under accession number 1370. *Setosphaeria monoceras* AGWH#11 assigned IMTECH accession number MTCC 5974 and NCIM accession number 1370 will be irrevocably and without restriction or condition released to the public upon the issuance of a patent. In a further aspect the present invention relates to a method for controlling growth of water hyacinth, comprising contacting the water hyacinth plants with the herbicide composition according to the invention.

In yet a further aspect the invention relates to use of an *Setosphaeria* strain for producing a herbicidal agent effective for controlling growth of water hyacinth plants. The strain used preferably is a strain having the characterizing features of *Setosphaeria* strain AGWH#11 as deposited at IMTECH under accession number MTCC 5974.

It is a further object of the present invention to provide the 18s rRNA sequence analysis showed 96% nucleotide similarity of the Fungi to *Setosphaeria monoceras*. (AGBIO designated AGWH#11/NCIM1370/MTCC 5974) but also indicated nucleotide variation of this fungus from other known genus of *Bipolaris*, Pleosporaceae, *Cochiliobolus, Alternaria* including an environmentally acceptable alternative to synthetic chemical herbicides for the control of weeds, such as Water hyacinth.

It is another object of the present invention to provide a herbicide composition for controlling Water hyacinth. Further objects of the invention relate to a method for controlling Water hyacinth.

SUMMARY OF THE PRESENT INVENTION

In a first aspect, the present invention provides a composition suitable for controlling water hyacinth, the composition comprising a herbicidal agent from a *Setosphaeria monoceras*. The *Setosphaeria monoceras* preferably is a strain having the characterizing features of *Setosphaeria monoceras* (MTCC 5974).

In a further aspect the present invention relates to a method for controlling growth of Water hyacinth, comprising the step of inoculating an area where water hyacinth is to be controlled with an effective amount of a herbicidal composition according to the invention.

In yet a further aspect the invention relates to use of a *Setosphaeria monoceras* for controlling growth of water Hyacinth. The strain used preferably is a strain having the characterizing features of *Setosphaeria monoceras* AGWH#11 as deposited at IMTECH and received accession number as MTCC 5974 and finally identified as *Setosphaeria monoceras*.

In yet a further aspect the invention relates to whole genomic study and molecular study of *Setosphaeria monoceras*

BRIEF DESCRIPTION OF THE DRAWINGS

FIG. 3 illustrates the macroscopic features of the strain in accordance with present invention;

FIG. 4 illustrates the microscopic features of the strain in accordance with present invention;

FIG. 5 and FIG. 6 illustrate base quality score distribution, left (R1) and right (R2) end of the paired end read for the sample in accordance with present invention;

FIG. 7 and FIG. 8 illustrate base composition distribution of left and right end of the paired end read sequence for the fungal sample in accordance with present invention;

FIG. 9 and FIG. 10 illustrate The GC distribution of left and right end of the paired end read sequence for the fungal sample in accordance with present invention;

FIG. 11 illustrate BLASTX E Value distribution for the fungal sample in accordance with present invention;

FIG. 12 illustrate annotated result of top 15 organisms found in BLASTX for the fungal sample in accordance with present invention;

FIG. 13 illustrate top 13 terms in biological function category identified using Gene ontology annotation for sample in accordance with present invention;

FIG. 14 illustrate top 13 terms in molecular function category identified using Gene ontology annotation for sample in accordance with present invention;

FIG. 15 illustrate top 13 terms in cellular component category identified using Gene ontology annotation for sample in accordance with present invention;

Table 1: Effect of AGWH#11 on Water hyacinth
Table 2: Biomass reduction of Water hyacinth
Table 3: Effects of AGWH#11 on detached leaves of Water hyacinth
Table 4: Response of crops, similar family and weed spices test for susceptibility
Table 5: Fungi collected from water hyacinth
Table 6: Pathogenicity of fungi collected from water hyacinth (tests applied to detached leaves of water hyacinth)
Table 7: Secondary screening of isolated strains
Table 8. Plants used in host-specificity test of isolates AGWH#11
Table 9: Comparisons of DNA sequences were performed between AGWH#11 sp. isolate
Table 10: Development of symptoms on water hyacinth due to infection with AGWH#11 during 20 days
Table 11: Bioassay of solvent extracted compound from AGWH#11

Table 12: Compatibility testing of various formulations of AGWH#11 by whole plant bioassay

DETAILED DESCRIPTION OF THE PRESENT INVENTION

The main object of this invention is to provide a novel herbicide effective against water hyacinth. Another object of the invention is to provide herbicide comprising cell free culture filtrate of *S. monoceras* MTCC 5974 with an additive or a carrier. Phylogenetic relationship of the selected species from the Genera *Setosphaeria monoceras*, based on 16S RNA genes, has been determined. During survey to Village AdaviRamanpalam, PenuballiMandal, Khammam District, Andhra Pradesh, the novel fungal species *Setosphaeria monoceras* was isolated from diseased Water hyacinth. Excised lesions were surface sterilized by immersion in 70% ethanol for 30 seconds and the excised lesions were rinsed in sterile water, placed in Petri plates containing Potato Dextrose Agar (PDA), and incubated 20 cm under fluorescent lights (12 hour diurnal period) for 3 days. Colonies of *Setosphaeria monoceras* were transferred to fresh PDA plates and subsequently transferred to PDA slants for storage. The isolates were grown on the Potato dextrose agar medium and stock cultures of these were maintained at Laboratory and given Lab number AGWH#11 and also deposited in the NCIM, Pune, India and given an accession number NCIM 1370 and under the Budapest Treaty IMTECH, Chandigarh, India, under accession number MTCC 5974.

The invention broadly pertains to a novel isolate *Setosphaeria monoceras* that exhibits host specificity toward Water hyacinth weeds. Colonies on potato dextrose agar are initially white to grayish brown and becomes olive green to black with a raised grayish periphery as it matures. The reverse is also darkly pigmented and olive to black in colour. The colony becomes mature within 5 days. The texture is velvety to wooly. The hyphae are septate and brown. Conidiophores (4.5-6 μm wide) are brown, simple or branched, geniculate and sympodial, bending at the points where each conidium arises from. This property leads to the zigzag appearance of the conidiophore. The conidia, which are also called poroconidia, are 3- to 6-celled, fusoid to cylindrical in shape, light to dark brown in color and have sympodial geniculate growth pattern. The poroconidium (30-35 μm×11-13.5 μm) is distoseptate and has a scarcely protuberant, darkly pigmented hilum. This basal scar indicates the point of attachment to the conidiophore. From the terminal cell of the conidium, germ tubes may develop and elongate in the direction of longitudinal axis of the conidium. The 18s rRNA sequence analysis showed 96% nucleotide similarity of the Fungi to *Setosphaeria* species but also indicated nucleotide variation of this fungus from other known Genus (FIG. 1). The pathogenicity of *Setosphaeria monoceras*, as a bioherbicide has been tested. Strain was tested to determine the host range with a bioherbicide. The plants were 4 weeks old and were treated with 1% developed formulation.

Accordingly, the present invention provides a herbicidal composition for controlling water hyacinth, the composition comprising a herbicidal agent from a *Setosphaeria monoceras*. The *Setosphaeria monoceras* preferably is a strain having the characterizing features of *Setosphaeria monoceras* AGWH#11. A characterizing feature of this strain is its 18s rRNA sequence. Sequence analysis showed 96% nucleotide similarity of AGWH#11 to *Setosphaeria mono-*

*ceras.* but also indicated nucleotide variation of this strain from other known species of the genus *Setospheria*. In addition AGWH#11 has surprising features in respect of herbicidal activity, in particular against water Hyacinth. The *Setosphaeria monoceras* having the characterizing features of *Setosphaeria monoceras* AGWH#11 most preferably is *Setosphaeria monoceras* AGWH#11 deposited as MTCC 5974 or NCIM1370.

In an embodiment of the present invention, the herbicidal agent may be a hyphal or a spore inoculum, such as a conidial inoculum. The term inoculum referring to an agent comprising fungal biomass. The inoculum may be viable or non-viable. A non-viable inoculum may be obtained by subjecting a viable inoculum to an inactivating treatment as is known in the art. Heat treatment may be suitably used for inactivating an inoculum. Hyphal and/or (conidia) spore inocula may be obtained from solid or liquid fermentations. A hyphal inoculum may be selected as a hyphal suspension. Similarly a (conidia) spore inoculum may be selected from a spore suspension.

Figure 2:
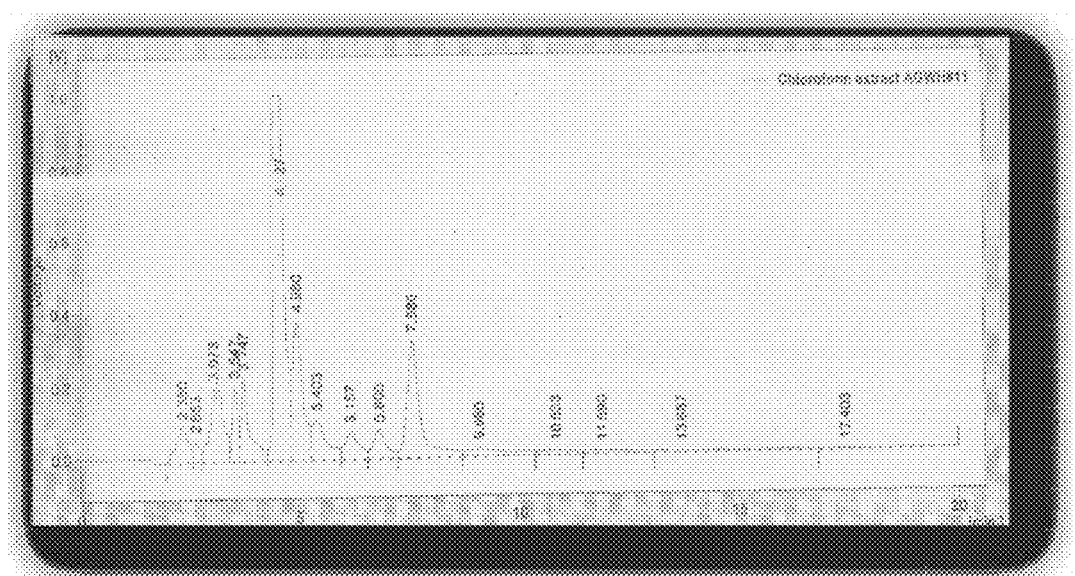
FIG. 2 illustrates a typical HPLC, C18 Reverse phase Column elution profile of a herbicidal agent (phytotoxin) in accordance with present invention.

In an embodiment of the present invention, the herbicidal agent may be culture broth (fermentation broth). Within the present invention the term culture broth refers to the liquid in which the fungus was grown. Culture broth may be used as it results from a liquid fermentation and may contain fungal biomass such as hyphal and/or (conidio) spore biomass. According to certain preferred embodiments the culture broth is at least partially purified. The term "at least partially purified" comprises partially purified. A partially purified culture broth results from performing a number of purification steps that increase the contents of certain compounds of the culture broth (while removing others). A partially purified culture broth remains a mixture of compounds. For example a partially purified culture broths may be cell free culture filtrate (CFCF) for example obtained by filtering-off the fungal biomass with any known means such as microfiltration. A partially purified culture broth may further be obtained by (organic) solvent extraction of certain compounds from the culture broth or from a CFCF obtained therefrom. According to certain embodiments the solvent is selected from hexane, Ethyl acetate, chloroform, methanol or mixtures therefrom. The selected solvent preferably comprises chloroform and most preferably is chloroform. When using chloroform as a solvent a potent herbicidal agent is obtained as is further detailed in the examples. The invention therefore further relates to a herbicidal agent obtainable by organic solvent extraction, in particular a chloroform extraction, of CFCF of the *Setosphaeria monoceras* used. The chloroform solvent extract may have the elution profile presented in FIG. 2 on HPLC C 18 profile. The herbicidal agent according to the invention will comprise a number of secondary metabolites. "A number of" within the present invention should be construed as meaning one or more, such as a plurality, for example 2-10 such as, 3-9, 4-8, 5-7, or 6. Secondary metabolites in the herbicidal agent may be further purified. According to certain embodiments the secondary metabolites are purified to >80% purity, such as >85%, >90%, >95%, >99% up to 99.9% purity.

The compositions and methods of the invention include the provision of application of cell free culture filtrate or their metabolites to produce a novel herbicidal agent. herbicide compositions may be prepared as a liquid formulation by suspending the broth, partially purified broth, such as cell free broth, crude or purified metabolites in an agriculturally acceptable carrier for application to the weed or the location where it is growing. For compositions of the invention, any agriculturally acceptable carrier can be used whether it is liquid or solid as long as it can be employed in agricultural or horticultural formulations and is preferably biologically inert. Exemplary agriculturally acceptable liquid carriers include, but are not limited to, water, surfactants, vegetable oils, and mineral oils. In a preferred embodiment, the agriculturally acceptable carrier for a liquid formulation is water, and the herbicidal agent comprises a cell free broth.

Herbicide compositions can also be prepared as granular formulations, flowable formulations, or wettable powder formulations by mixing with an agriculturally acceptable carrier, which is then applied to weed.

Suitable agriculturally acceptable solid carriers include mineral powders, such as clay, talc, bentonite, calcium carbonate, diatomaceous earth and white carbon; vegetable flours such as soybean flour and starch, and some polymers such as polyvinyl alcohol and polyalkylene glycol.

According to preferred embodiments in the formulation a surfactant, such as a Tween 80, Triton X, Paraffin oil and Tween 20 are combined with an antibiotic agent. As is shown in the experimental section such a combination results, increase the activity of water hyacinth control. According to other preferred embodiments in the formulation a mineral oil, such as paraffin oil, is combined with an antibiotic (antimicrobial). As is shown in the experimental section such a combination results in a surprising increase of the activity of water Hyacinth control. Streptomycin, Ampilox, Azithromycin may be selected from these antibiotics. In a general formulating agents can be added in an amount of 0.2-0.9% w/w, such as 0.3-0.8%, 0.4-0.7%, 0.4-0.6%, such as about 0.5% w/w to the herbicidal agent. Antimicrobials may be added in an amount of 0.05-0.5% w/w such as 0.06-0.4%, 0.07-0.3%, 0.08-0.3%, 0.09-0.3%, 0.1-0.3% such as about 0.2% w/w to the herbicidal agent.

Further in another embodiment of the present invention, the present composition further comprises a nutrient source for the *Setosphaeria monoceras* strain. The nutrient may be selected from vegetable flours such as soybean flour and starch and added in amounts of 0.5% to the culture medium A further aspect of the invention relates to a method of controlling weeds, in particular water Hyacinth and related species. The method comprises_contacting_water hyacinth with the composition according to the invention, containing the herbicidal agent. The composition of the invention can be applied to the water Hyacinth weed for contacting by spraying a liquid formulation at weeds. The amount sprayed preferably is sufficient to substantially coat the leaves of the weed. One application may be sufficient to reduce current growth; however, repeat applications may be necessary if regrowth of the plant occurs from resistant or below surface structures. Also the method of the present invention may be used in addition to or in conjunction with other control measures.

As such the method is for suppressing or preventing growth of water Hyacinth and the method comprises the step of contacting water Hyacinth with a composition of the invention. Details of the technical features of the composition of the invention have been discussed above. As the skilled person will understand the composition of the invention will be inoculated in an amount sufficient to bring an effect, in particular control (reduction or inhibition) of growth of water Hyacinth. It is within the ambit of the knowledge and skill of the skilled person to determine effective amounts. According to certain embodiments effective amounts may be in the range of 10 ml of formulated cell free culture broth added to 1 liter of water for application. About 1.0 to 1.5 liter per acre is applied by method of spraying and the like. The herbicide of the invention may be formulated by suspending in water spores obtained by mass-culturing, but the formulation method is not limited to this one. In this method, the spore concentration is appropriately 2×108 spores/ml but not limited to this range. In suspending spores in water, adjuvants such as a surfactant and a spreader may be added. The *Setosphaeria monoceras* strain which is the major agent may be a fresh strain immediately after fermentation. Alternatively, a once stored strain may be used after renaturing with water or the like. As a method for storing, well known methods for storing strain such as ultra low temperature storing (−10 DEG C.), vacuum lyophilization or the like may be used.

In certain embodiments of the present invention, the inoculation is carried out at post-emergent stage of the water Hyacinth weed. According to some embodiments of the method of the invention water hyacinth biomass may be reduced, for example with mechanical means, such as by mechanically removing water Hyacinth biomass.

A further aspect of the invention relates to the use of a *Setosphaeria monoceras* strain, preferably a strain having the characterizing features of *Setosphaeria monoceras* strain AGWH#11 for producing a herbicidal agent effective for controlling growth of water Hyacinth. The technical features of the herbicidal agent have been discussed above in connection to the discussion of the composition of the invention. Similar to what is discussed for the composition of the invention, the herbicidal agent may be selected from a hyphal inoculum, a spore inoculum, preferably a conidial inoculum, culture broth, preferably an at least partially purified culture broth, secondary metabolites.

Yet a further aspect of the invention relates to a herbicidal agent obtainable by a method comprising chloroform extraction of Cell Free Culture Filtrate (CFCF) of a *Setosphaeria monoceras*. In the method the CFCF is provided, preferably by culturing the selected strain in a liquid culture and producing a CFCF from the culture broth. Next a chloroform extraction is performed on said CFCF. The extraction of metabolites has been completed. One liter of broth medium was inoculated and incubated for approximately 14 days at 28° C. Chloroform with similar volume was added to the supernatant fluid. The crude metabolites were recovered by carefully pouring off aqueous layer. A extraction of culture supernatant fluid with chloroform yielded 9.5 gm of crude metabolites. The *Setosphaeria monoceras* preferably is a strain having the characterizing features of *Setosphaeria monoceras* AGWH#11.

The following examples are given by the way of illustration of the present invention and therefore should not be construed to limit the scope of the present invention.

Example 1

Figure 1:
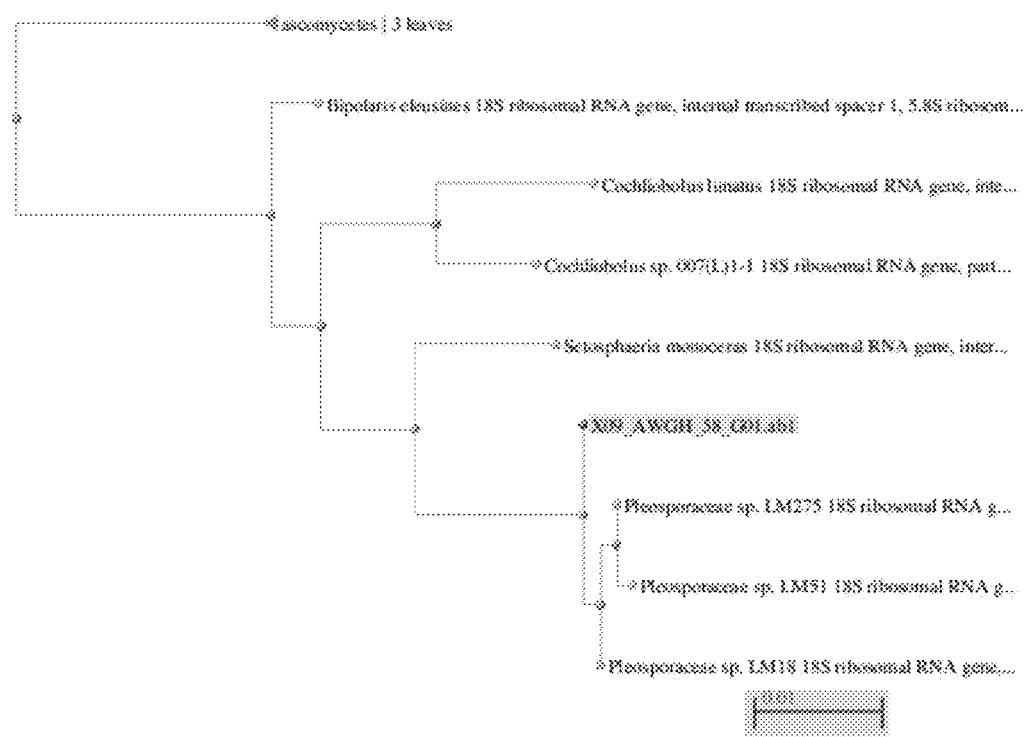
FIG. 1 illustrates phylogenetic relationship of fungi to selected species from the other genera based on 16S RNA genes in accordance with present invention.

Survey, Isolation and Fungal Classification:

The various place of Andhra Pradesh has surveyed for collection of infected parts of water hyacinth (petiole and leaf). Samples were transported to the laboratory in clean plastic bags and stored at 4° C. until examined. Stored plant parts were scrubbed under running water to remove surface debris, dissected into small segments (approximately 1×1 cm), and surface-sterilized by sequential immersion in 96% ethanol for 30 seconds, 14% hypochlorite for 30 seconds and rinsed in sterile water for 1 min. Surface-sterilized segments from petioles and leaves were placed on Potato Dextrose plate supplemented with 0.5 mg streptomycin. The plates were incubated for 7 days at 25° C. temperature. The isolated and pure cultures were obtained. Identification of the different fungal genera was based on morphological characteristics of each growing microbial colony. Fungi having distinctive characteristics of saprophytes (i.e. rapid growth and sporulation on PDA plates and isolates in the genera *Penicillium, Aspergillus*, and *Trichoderma* were excluded from further consideration after their initial isolation. The retained necrotrophic fungal isolates were identified. The fungal isolates were stored at Lab. The symptoms initially appeared as small necrotic spots and developed into a leaf blight spreading over the leaf surface and the petiole. The infecting fungi (46 isolates of filamentous fungi) were identified as belonging to 7 known genera (Table 7) on the basis of their morphological characteristics and the arrangement and structure of their conidia. The cell free filtrate of a 10 day old culture of the candidate fungus AGWH#11 was found to be equally active as its spore suspension in inciting necrosis of water hyacinth tissue. This indicated that the fungus elaborates toxic metabolites in the culture broth which usually induces such syndrome resulting in destruction of the cellular contents and collapse of the cell walls of water hyacinth. The phytotoxin was extracted from a cell free culture filtrate of AGWH#11, grown on liquid media. The cell free filtrate was extracted successively with solvent hexane, Ethyl acetate, Chloroform and methanol (FIG. 1). Phytotoxic compounds showing more toxicity in chloroform fraction

TABLE 1

Fungi collected from water hyacinth

| Pathogens | Symptoms | Accession number |
|---|---|---|
| *Setosphaeria monoceras* Total = 07 | Leaf spot | AGWH04 AGWH05 AGWH11 AGWH20 AGWH56 AGWH 58 AGWH61 |
| *Alternaria* sp. Total = 10 | Leaf spot | AGWH01 AGWH16 AGWH 59 AGWH60 AGWH69 AGWH70 AGWH 75 AGWH76 AGWH77 AGWH79 |
| *Fusarium* sp. Total = 09 | Leaf spot | AGWH07 AGWH08 AGWH10 AGWH14 AGWH62 AGWH65 AGWH66 AGWH67 AGWH68 |
| *Phoma* sp. Total = 05 | Leaf spot | AGWH02 AGWH03 AGWH06 AGWH63 AGWH64 |
| *Curvularia* sp. Total = 03 | Leaf spot | AGWH12 AGWH15 AGWH18 |
| *Pestalotia* sp. Total = 04 | Leaf spot | AGWH11 AGWH13 AGWH19 AGWH21 = 04 |
| *Colletotrichum* sp. Total = 06 | Leaf spot | AGWH09 AGWH71 AGWH72 AGWH73 AGWH74 AGWH78 |

Example 2

Pathogenicity Test:

During experiments, the initial conidial inoculum was taken from petri-dish cultures on PDA medium, preserved at 4° C. for no more than 6 months, and then sub-cultured at 25° C. on culture media before use. Healthy water hyacinth plants were collected from natural infestations and maintained in greenhouse of Lab. In a preliminary screen, the fungal pathogens were tested for their effects on leaf fragments cut from healthy_water hyacinth plants. Each fragment was placed on the surface of a petri plate containing blot paper with water. Spore suspensions (20 ml) were prepared from the fungal isolates (2×10 spores ml with Tween 20), and manually sprayed manually onto a set of leaf fragments. After inoculation, the petri plates were immediately sealed with Parafilm to prevent water loss and incubated at 25° C. with a 16-h photoperiod for 4 weeks.

The plants were rated for disease symptoms. The experiment was repeated three times. Leaf fragments and plants were rated for disease symptoms including leaf spots, leaf lesions, and leaf death respectively. The impact of the pathogens was determined by assessing the type of damage (disease severity, DS). DS was determined for each leaf on a scale of 0=no effect; 1=up to 20% leaf area necrotic; 2=Up to 40% leaf area necrotic; 3=up to 60% leaf area necrotic; 4=up to 80% leaf area necrotic; 5=Up to 100# leaf area necrotic.

In the preliminary screen, all 44 fungal isolates were tested in vitro on leaf fragments of water hyacinth plants. All the fungal isolates were able to infect the plant and produce some disease symptoms (Table 2). Disease started as small necrotic spots and developed into a leaf blight that tended to spread over the leaf, however, only nine pathogens produced symptoms over more than 50% of the total foliar area by the end of the 4-week incubation period. These were: AGWH#11 (*Setosphaeria monoceras*), AGWH20 (*Setosphaeria monoceras*), AGWH06 (*Phoma* sp.), AGWH15 (*Curvularia*_sp), AGWH21 (*Pestalotia* sp.), AGWH 16 (*Alternaria* sp.), AGWH8 (*Fusarium* sp.), AGWH10 (*Fusarium* sp), and AGWH9 (*Colletotrichum* sp.). Disease severity values were calculated over the 4-week period for all 46 isolates (Table 3). The DS values at the end of the experiment for the nine most damaging pathogens were: 80-100% for *Setosphaeria monoceras* isolates AGWH11 and AGWH 20 respectively, 60% to 79% for *Alternaria* sp. isolates AGWH16, AGWH08, AGWH10 for *Fusarium* sp. isolates, AGWH06 for *Phoma* sp. AGWH09 for *Collectotrichum*, AGWH15 for *Curvularia* AGWH21 for *Pestalotia* respectively.

TABLE 2

Pathogenicity of fungi collected from water hyacinth (tests applied todetached leaves of water hyacinth)

| Pathogens | Symptoms | Accession number | Detached leaf bioassay |
|---|---|---|---|
| *Setosphaeria monoceras* Total = 07 | Leaf spot | AGWH04 | 2 |
| | | AGWH05 | 2 |
| | | AGWH11 | 5 |
| | | AGWH20 | 4 |
| | | AGWH56 | 2 |
| | | AGWH 58 | 2 |
| | | AGWH61 | 2 |
| *Alternaria* sp. Total = 10 | Leaf spot | AGWH01 | 1 |
| | | AGWH16 | 3 |
| | | AGWH 59 | 2 |
| | | AGWH60 | 2 |
| | | AGWH69 | 2 |
| | | AGWH70 | 2 |
| | | AGWH 75 | 2 |
| | | AGWH76 | 2 |
| | | AGWH77 | 2 |
| | | AGWH79 | 2 |
| *Fusarium* sp. Total = 09 | Leaf spot | AGWH07 | 2 |
| | | AGWH08 | 3 |
| | | AGWH10 | 4 |
| | | AGWH14 | 2 |
| | | AGWH62 | 2 |
| | | AGWH65 | 2 |
| | | AGWH66 | 2 |
| | | AGWH67 | 2 |
| | | AGWH68 = 09 | 2 |
| *Phoma* sp. Total = 05 | Leaf spot | AGWH02 | 1 |
| | | AGWH03 | 1 |
| | | AGWH06 | 3 |
| | | AGWH63 | 2 |
| | | AGWH64 = 05 | 2 |
| *Curvularia* sp. Total = 03 | Leaf spot | AGWH12 | 1 |
| | | AGWH15 | 4 |
| | | AGWH18 = 03 | 1 |
| *Pestalotia* sp. Total = 04 | Leaf spot | AGWH11 | 2 |
| | | AGWH13 | 2 |
| | | AGWH19 | 1 |
| | | AGWH21 = 04 | 3 |
| *Colletotrichum* sp. Total = 06 | Leaf spot | AGWH09 | 3 |
| | | AGWH71 | 2 |
| | | AGWH72 | 2 |
| | | AGWH73 | 2 |
| | | AGWH74 | 2 |
| | | AGWH78 | 2 |

Key Abbreviation for detached leaf rating 0=no effect; 1=up to 20% leaf area necrotic; 2=Up to 40% leaf area necrotic; 3=up to 60% leaf area necrotic; 4=up to 80% leaf area necrotic; 5=Up to 100# leaf area necrotic. The strain AGWH 06, 08, 09, 10, 11, 15, 16, 20 & 21 caused more than 50% LAD, selected for secondary screening.

Example 3

Secondary Screening of Strain:

The second screening was carried out using the nine fungal isolates displaying the highest herbicidal activity in vitro. Among them, only isolates AGWH#11 (*Setosphaeria monoceras*) showed a DS of at least 100% after a 96 hr incubation (Table 3). The DS was ranged from 40% to 47% for isolate *Alternaria* sp. isolates AGWH16, AGWH08, AGWH10 for *Fusarium* sp. isolates, AGWH06 for *Phoma* sp. AGWH09 for *Colletotrichum*, AGWH15 for *Curvularia* AGWH21.

TABLE 3

Secondary screening of isolated strains

| | | % Disease severity | | | |
|---|---|---|---|---|---|
| SN | Fungal isolates | 24 hrs | 48 hrs | 72 hrs | 96 hrs |
| 1 | AGWH06 | 1 | 2 | 2 | 2 |
| 2 | AGWH 08 | 1 | 1 | 1 | 1 |

TABLE 3-continued

Secondary screening of isolated strains

| SN | Fungal isolates | % Disease severity | | | |
|---|---|---|---|---|---|
| | | 24 hrs | 48 hrs | 72 hrs | 96 hrs |
| 3 | AGWH 09 | 1 | 2 | 2 | 2 |
| 4 | AGWH 10 | 1 | 2 | 3 | 3 |
| 5 | AGWH 11 | 1 | 3 | 5 | 5 |
| 6 | AGWH15 | 1 | 2 | 2 | 2 |
| 7 | AGWH16 | 1 | 2 | 2 | 3 |
| 8 | AGWH20 | 1 | 2 | 2 | 2 |
| 9 | AGWH21 | 1 | 2 | 3 | 3 |

Key Abbreviation for detached leaf rating 0=no effect; 1=up to 20% leaf area necrotic; 2=Up to 40% leaf area necrotic; 3=up to 60% leaf area necrotic; 4=up to 80% leaf area necrotic; 5=Up to 100# leaf area necrotic.

The present results highlight AGWH#11 as potential bioherbicide for use in controlling water hyacinth.

Example 4

Host Specificity Tests

The host specificity of the selected fungi also was tested in greenhouse. Non-aquatic plants were grown in pots filled with aseptic commercialized soil free of any fungi. The experiment was replicated three times. Inoculation of the water hyacinth ecotypes and crop plants was done by spraying suspension containing $2 \times 10^6$ spores/ml. The plants were monitored for disease symptoms. This led us to test the host ranges of isolate AGWH#11. Table 4 and FIG. 1 show the results obtained when strain was delivered crop-plants and weeds. Four weeks after application of either isolate, water hyacinth showed lesions on their leaves, whereas none of the other plants showed any signs of infection. Based on our results, these fungal isolate would not be expected to affect economically important plants and should thus be viewed as potential candidates for managing water hyacinth infestations.

TABLE 4

Plants used in host-specificity test of isolates AGWH#11 (+ means shows infection).

| Plants testes | Phytotoxicity |
|---|---|
| Chilly | − |
| Tomato | − |
| Brinjal | − |
| Water hyacinth | + |
| Grass | − |

Example 5

Morphological Characteristics:

As per morphological analysis, indigenous strain AGWH#11 (NCIM 1370) isolated from Water hyacinth infected leave is Setosphaeria monoceras. The AGWH#11 (Indian classification as Drechslera sp) classified as Setosphaeria monoceras in Japan and Australia.

Macroscopic Features

Setosphaeria monoceras. colonies grow rapidly, reaching a diameter of 3 to 9 cm following incubation at 25° C. for 7 days on potato dextrose agar. The colony becomes mature within 5 days. The texture is velvety to woolly. The surface of the colony is initially white to grayish brown and becomes olive green to black with a raised grayish periphery as it matures. The reverse is also darkly pigmented and olive to black in color.

Microscopic Features

The hyphae are septate and brown. Conidiophores are brown, simple or branched, geniculate and sympodial, bending at the points where each conidium arises from. This property leads to the zigzag appearance of the conidiophore. The conidia, which are also called poroconidia, are 3- to 6-celled, fusoid to cylindrical in shape, light to dark brown in color and have sympodial geniculate growth pattern.

Example 6

Molecular Analysis

The present study was designed to provide a taxonomic position of the isolate AGWH#11 at the species level, using DNA sequence comparisons.

Internal transcribed spacers 1 and 2 [ITS-1 and 2] and 5.8 S regions of the nuclear ribosomal DNA [rDNA] transcriptional unit were performed_between isolate AGWH#11 and the closest species or isolates for which sequences were available. Comparison of the ITS rDNA gene showed that AGWH#11 isolate was 99% identical to 2 other isolates (Table 5). Concerning the study, isolate AGWH#11 showed 96% identity with Setosphaeria monoceras. Similarly to the ITSrDNA gene, the 18S rDNA gene sequence of isolate AGWH#11 showed than a 91% identity with 4 different Alternaria sp. Similarly to the ITSrDNA gene, the 18S rDNA gene sequence of isolate AGWH#11 showed than a 93% identity with Cochliobolus lunatus and one other Cochliobolus sp showing 94% similarity. Similarly it is showing 95% identity with Bipolaris elecusines.

TABLE 6

Comparisons of DNA sequences were performed between AGWH#11 sp. isolate

| Organism | GenBank Accession(s) | % identity (bp) |
|---|---|---|
| Setosphaeria monoceras | DQ337380 | 96 |
| Bipolariseleusines | DQ337382 | 95 |
| Pleosporaceae sp | EF060604 | 99 |
| Pleosporaceae sp | EF060407 | 99 |
| Cochlioboluslunatus | DQ337381 | 93 |
| Pleosporaceae sp | EF060433 | 99 |
| Cochliobolus sp. | FJ235087 | 94 |
| Alternariamultirostrata | AM237287 | 91 |
| Alternariacichorii | AM237286 | 91 |
| Alternariajesenskae | AM237084 | 91 |
| Alternariapassiflorae | AM237288 | 91 |

DNA sequence comparisons and morphological description provided enough evidence Setosphaeria monoceras. isolate AGWH#11 belonged to the Setosphaeria genus and was distinct enough from any other known Setosphaeria monoceras ecies. A specimen culture has been deposited in the NCIM under the accession number 1370 and MTCC 5974 deposited in IMTECH.

Example 7

Bioassay of AGWH#11 Cell Free Culture Filtrate:

In the present investigation, Genus AGWH#11 was found to be strong in inciting pathogenesis in the plant. The cell free culture filtrate of AGWH#11 was capable of inciting the same syndrome as its spore's suspension. The active substance of CFCF was study by HPLC. The separated active compound showing necrosis of leaves. This substance appears to hold some promise as a possible biocontrol agent for water hyacinth.

The method involves inoculating *Setosphaeria monoceras*, as a bioherbicide. *Setosphaeria* was modified Potato sucrose broth (PSB) medium grown at 28° C.±1° C. under in one liter flasks containing 250 ml modified medium. The culture filtrates were collected by successive passage through Whatman No. 1 filter paper. The culture filtrate may be combined with a liquid carrier, such as paraffin oil and non phytotoxic surfactant such as 2% glycerol. Hyphae and/or conidia from the cultures of *Setosphaeria monoceras* has killed by heat treatment and mix 0.2% sodium benzoate as microcide into culture broth. The application rate should be in the range of from about 10 ml of product mix into 1 liter of water to Water hyacinth plant. The attack of the bioherbicide on Water hyacinth is manifested by the appearance of brown lesions or necrotic areas, followed by wilting and death of the plant. The result of this test is depicted in Table 10.

TABLE 7

Development of symptoms on water hyacinth due to infection with AGWH#11 during 20 days

| Days after infection | Description of syndrome |
|---|---|
| 2 | No appreciable symptoms |
| 5 | Enlarged spots of yellow color |
| 7 | Enlarged spots of deep yellow colour with brown colored margins |
| 10 | The affected areas turn necrotic and appearance of blotchy lesions and or leaf blights. |
| 12th | The syndrome extend to petioles and or stolon of the plant, some parts get dried; partial defoliation while other get dried. |
| 20 | The weed individuals disappeared and the contents of nearly all pots appeared to turn into dirty or dark brown colored fluid. |

Example 8

Bioassay with Detached Leaves:

Detached Water hyacinth leaves were used to test the, biological activities of cell free filtrates, crude filtrate and partially purified toxin. Detached leaves were placed on moistened filter paper inside 9-cm diameter sterile Petri plates. The inocula of crude filtrates, cell- and spore-free filtrates, and the partially purified phytotoxin were applied to the leaves with micropipets. Ten leaves were used for each treatment. Control leaves received distilled water. The plates were sealed with parafilm and incubated at Room temperature under 12 h light conditions. The phytotoxic effects on the treated excised leaves were evaluated visually for damage for 5 days. The result of this test is depicted in Table 3.

TABLE 8 effects of AGWH#11 on detached leaves of Water hyacinth

| Phytotoxin | Concentration (μl/ml) | Phytotoxicity |
|---|---|---|
| Cell free filtrate | 100 | + |
| Crude filtrate | 10 | + |
| HPLC purified | 0.2 | + |
| Control | 100 | − |

The phytotoxic damage was evaluated visually for 5 days.
− = no phytotoxic effects, + = phytotoxic effects.

Example 9

Bioassay of Solvent Extracts Crude Metabolites:

Detached leaf of water hyacinth with solvent extract metabolites was tested. Phytotoxic compounds were detected in the hexane and ethyl acetate fraction (Table 11). Chloroform has showing 100% toxicity.

TABLE 9

Bioassay of solvent extracted compound from AGWH#11

| | Phytotoxicity | | | | |
|---|---|---|---|---|---|
| items | Control | Methanol extract | Hexane extract | Chloroform extract | Ethyl acetate Extract |
| Detached leaf | 0 | + | ++ | ++++ | ++ |

Phytotoxic activity indexing was on a scale
0 = 0 treated with water, no lesion;
+ = 5% diam;
++ = 25%;
+++ = 75%
++++ = 100%, Many necrotrophic plant pathogenic fungi belonging to the class of Dothideomycetes produce phytotoxic metabolites and peptides that are usually required for pathogenicity. Phytotoxins that affect a broad range of plant species are known as non-host-specific toxins (non-HSTs), whereas HSTs affect only a particular plant species or more often genotypes of that species. For pathogens producing HSTs, pathogenicity and host specificity are largely defined by the ability to produce the toxin, while plant susceptibility is dependent on the presence of the toxin target. Non-HSTs are not the main determinants of pathogenicity but contribute to virulence of the producing pathogen. Dothideomycetes are remarkable for the production of toxins, particularly HSTs because they are the only fungal species known so far to produce them.

Example 10

Production and Purification of Phytotoxin and High Performance Liquid Chromatography:

*Setosphaeria monoceras* was grown at 28° C.±1° C. under in one liter flasks containing 250 ml modified PSB medium. The sterile media was inoculated with 1 ml of a spore suspension of fungus, shaken gently, and incubated as standing cultures for 14 days. The culture filtrates were collected by successive passage through Whatman No. 1 filter paper, and a Sartorius membrane filter (0.20 μm). The culture filtrate which has been passed through the Sartorius membrane filter. Cell free culture filtrate extracted with chloroform to get to solvent extract. The chloroform extract sterile filtrates were stored at 4° C. depending on assay or fractionation. High Performance Liquid Chromatography (HPLC) was performed using methanol: water (0-100% gradient for 30 minutes) as solvent system in C18 reverse phase column. A typical HPLC, C18 reverse phase column elution Profile of partially purified Toxin (FIG. 1).

The separation of various peaks of AGWH#11 metabolites and its chemical characterization will be characterized by NMR and GC MS study and it will be added to the results

Example 11

Formulation Studies:

Formulation refers to the process of blending of secondary metabolite or microbe with inert carriers to alter their physical characteristics to enhance its shelf life and field performance. Formulation involves the use of formulants which include: adjuvants, surfactants, wetting agents, spreaders and preservative. The use of formulative for biological control is a relatively new application of technology that is well known to the chemical herbicide industry. Adjuvant increases the efficacy of post emergence herbicides by increasing the wettability of the target surface as they reduce surface tension. Adjuvants are also known to enhance penetration. In order to investigate the compatibility of the phytotoxin produced by the test fungus with various formulants were tested. Thus, the objective of the present study was to evaluate the compatibility of different formulants as singlets and in combinations against the target weeds.

To test the compatibility of the toxin synthesized by the pathogen seven formulating agents namely, Tween-20, Tween-80, Ek Bond soyabean oil, mustard oil, coconut oil, groundnut oil, glycerol were used. Formulating agents were added @ 0.5% to the CFCF containing phytotoxin with antimicrobial 0.2% and compatibility was determined by whole plant bioassay.

In order to investigate the compatibility of the phytotoxins produced by the test fungus various formulants were tested. Data represented in Table 12, the phytotoxic damage studies clearly show that the most compatible formulant was Parafin oil with preservative followed by coconut oil, Ek bond, Tween-80, Tween-20 and glycerol. On the basis of results obtained above, it can be concluded that the secondary metabolites of AGWH#11 possess high herbicidal potential with paraffin oil and can be developed as potential herbicides for the management of water hyacinth.

TABLE 10

Compatibility testing of various formulations of AGWH#11 by whole plant bioassay

| SN | Adjuvant | Water hyacinth phytotoxic disease rating | | |
|---|---|---|---|---|
| | | 3 days | 5 days | 10 days |
| 1 | Control a | 0 | 0 | 0 |
| 2 | Control b | 0 | 0 | 0 |
| 3 | Coconut oil | 2 | 2 | 2 |
| 4 | Tween 20 + antimicrobial | 3 | 3 | 4 |
| 5 | Paraffin oil + antimicrobial | 4 | 5 | 5 |
| 6 | Soybean oil + antimicrobial | 2 | 2 | 2 |
| 7 | Glycerol + antimicrobial | 2 | 2 | 2 |
| 8 | Mustard oil + antimicrobial | 2 | 2 | 2 |
| 9 | EK bond + antimicrobial | 2 | 2 | 3 |
| 10 | CFCF alone + antimicrobial | 2 | 2 | 2 |

Control a—Unmetabolised growth medium
Control b—Sterilized Distilled Water;
Amount of CFCF containing phytotoxin employed = 10 ml/plant Plant Disease Rating (PDR)

0-1=slight curling & wilting; 1-2=slight chlorosis; 2-3=marked chlorosis, slight necrosis; 3-4=high necrosis and marked chlorosis; 4-5=acute necrosis and marked chlorosis; 5=acute chlorosis and acute necrosis leading to death of seedling.

Example 12

Biomass Reduction Study:

Whole plant pathogenicity test was contact with Glasshouse trail to test developed bioherbicide. The purpose of the investigations was to determine the efficacy of 1% concentrations of *S. monoceras* on Water hyacinth plants after application. The cell free cultures filtrate of *S. monoceras* formulated with 0.2% sodium benzoate. The application rate should be in the range of from about 10 ml of formulated product mix into 1 liter of water to Water hyacinth plant. The attack of the product on Water hyacinth is manifested by the appearance of brown lesions or necrotic areas, followed by wilting and death of the plant. The results showed a great reduction in dry weight of biomass with more than 80% irrespective of the 1% concentration on plants of the leaf stage 1-3 and 5-7. Mortality was reached complete within 7 days. Obtained results illustrate that the application of product with 10 ml/1 liter of water on all treatments give a great reduction of biomass and adversely affects regeneration of the plants. The result of this test is depicted in Table 11.

TABLE 11

Biomass reduction of Water hyacinth

| SN | Weight Before application (gm) O days | Weight After application (gm) | | | | | | |
|---|---|---|---|---|---|---|---|---|
| | | $1^{st}$ days | $2^{nd}$ day | $3^{rd}$ day | $4^{th}$ day | $5^{th}$ day | $6^{th}$ day | $7^{th}$ day |
| Control | 62.5 | 62.5 | 62.5 | 62.5 | 62.5 | 62.5 | 62.5 | 62.5 |
| Weed 1 | 60.5 | 51.5 | 42.5 | 41.5 | 29.5 | 22.5 | 19.5 | 18.0 |
| Weed 2 | 75.0 | 66.0 | 56.0 | 55.0 | 36.0 | 29.0 | 23.0 | 20.0 |
| Weed 3 | 60.0 | 50.0 | 49.0 | 47.0 | 33.0 | 26.0 | 21.0 | 17.0 |
| Weed 4 | 40.0 | 31.0 | 23.0 | 21.0 | 13.0 | 9.0 | 7.0 | 5.0 |
| Weed 5 | 100.0 | 90.0 | 87.0 | 82.0 | 60.0 | 42.0 | 40.0 | 31.0 |
| Weed 6 | 32.0 | 22.0 | 13.0 | 11.0 | 7.0 | 5.0 | 4.0 | 4.0 |

Whole Genome Study

*Setosphaeria monoceras* DNA was extracted by Scigenom developed protocol and the sequencing library was prepared using Illumina paired end DNA sample prep kit. Sequencing was performed using Illumina Genome Analyser. Short reads were assembled de novo using velvet and assembly quality was improved by a pipeline including two alternate assemblers Edena and Minimus.

*Setosphaeria monoceras* strain AGWH#11 (NCIM 1370) was sequenced by a whole genome shotgun approach using the Illumina Genome Analyzer. Fastq quality check, De novo assembly of genome study, Gene prediction, ORF annotation and Blastx search performed.

Fastq quality check and filtering results are shown in Table 12

TABLE 12

Raw read summary

| Sample | AGWH 11 |
|---|---|
| Number of paired end reads | 25,892,527 |
| Number of bases (Gb) | 5.17 |
| GC % | 52.83 |
| Percentage of data >= Q30 | 80 |

Fastq quality check involved checking of quality parameters for the sequence obtained from sequencer. Base quality score distributions, average base content per read and GC distribution in the reads were performed for an input fastq file. The base quality score distribution, the quality of left (R1) and right (R2) end of the paired end read for the sample is shown in FIG. 5, 6. The x-axis represents sequencing cycle and y axis represent the phredquality score of bases. It was observed that average base quality was above Q30 (error probability >=0.001) for more than 80% of bases.

Base composition distribution of left and right end of the paired end read sequence is shown in FIGS. 7 and 8. The x-axis represents sequencing cycle and y axis represents nucleotide percentage. We observed bias in the base composition towards the beginning of reads. Biasing in sequence composition is generally observed in NGS experiments.

The GC distribution of left and right end of the paired end read sequence were performed (FIG. 9, 10). The x-axis represents average GC content in the sequence and y axis represents total percentage of reads. The average GC content of the reads in the sample followed a normal distribution.

The fastq files were trimmed before performing Denovo-contigs assembly. Scigenom scientists have trimmed three bases from the beginning and two bases from the end of the reads. Summary of the trimmed reads are provided in Table 13.

TABLE 13

Trimmed read summary for samples AGWH#11

| Sample | AGWH#11 |
| --- | --- |
| Number of paired end reads | 25,892,527 |
| Number of bases (Gb) | 4.92 |
| Read length | 2x 95 bp |

Further, filtered out reads that were contained with illumine adapter. Kmer Genie used to predict the optimal k value and assembly size. KmerGenie results are recorded in Table 14.

TABLE 14

KmerGenie Results

| Sample | AGWH#11 |
| --- | --- |
| Predicted best k | 63 |
| Predicted Assembly size | 35,117,793 |

Various assembled independent contigs are used to integrate the contigs. For AGWH#11 the final assembly had 150 contigs and the longest contig was 1261505 bp long. The assembly statistics is provided in Table 15.

TABLE 15

Assembly Statistics for contigs

| Assembler | Min | Max | Mean | N50 | Total contigs | Sum of length of all contigs |
| --- | --- | --- | --- | --- | --- | --- |
| AS | 198 | 1119830 | 23715.43 | 319829 | 1486 | 35241127 |
| Edena | 142 | 394286 | 45948.5 | 94664 | 746 | 34277582 |
| SOAPdenovo | 66 | 284116 | 3610.24 | 59318 | 9833 | 35499493 |
| Velvet | 125 | 191558 | 6111.9 | 42794 | 5745 | 35112848 |
| MaSuRCa | 300 | 227951 | 15356.7 | 5446 | 2295 | 35243629 |
| CISA | 3140 | 1261505 | 236557.7 | 510532 | 150 | 35483656 |

For gene prediction and Annotation, the predicted ORFs from the contigs for the fungal sample AGWH 11 using Augustus method. Compared to gene prediction for AGWH11, we have used trained data from *Aspergillus nidulans* and *Neurospora crassa* to predict ORFs independently. We found 13, 950 unique ORFs in sample AGWH#11 from these predictions. The predicted ORFs were annotated using Scigenom in house pipeline (CANoPI-Contig Annotator) for de novo assembly. The steps for annotation of ORFs are comparison with NCBI database using BLASTX program, Organism annotation, gene and protein annotation to the matched ORFs, Gene ontology annotation and pathway annotation.

The predicted ORFs were compared with NCBI non redundant protein database using BLASTX program. Matches with E value <=1e−5 and similarity score >=40% were retained for further annotation. BLASTX summary is provided in Table 16. For Sample AGWH#11 overall we found 13,602 (97.38%) of predicted ORFs have at least one hit in NCBI database.

TABLE 16

BLASTX and UniProt Summary

| Categories | AGWH11 |
| --- | --- |
| Number of ORFs | 13,967 |
| Number of ORFs with significant BLASTX match | 13,400 |
| Number of ORFs with UniProt annotation | 13,380 |

The BLASTX search E value distribution is provided in FIG. 11. Around 91% of the ORFs found using BLASTX for the sample had confidence level of at least 1e−50, which indicated high protein conservation. 91% of the predicated ORFs found using BLASTX had similarity of more than 60% at protein level with the existing protein at NCBI database in Sample AGWH#11.

For organism annotation the top BLASTX hit of each ORF was studied and the organism name was extracted. The top 15 organism found in the annotation for the sample shown in FIG. 12.

Majority of the top BLASTX hit belong to *Setosphaeria turica* for this sample.

For gene and protein annotation, the predicted protein from BLASTX was annotated against NCBI, UniProt pathway and other databases. Among the total significant BLASTX hit ORFs 13, 380 ORFs were annotated using UniProt database. For remaining BLASTX hit NCBI predicted protein annotation were provided. The complete annotation were divided into following three categories (Table 17).

TABLE 17

Annotation status

| Sample | AGWH11 |
| --- | --- |
| Number of ORFs with no significant BLASTX hit | 365 |
| Number of ORFs with significant BLASTX hit but no UniProt information | 20 |
| Number of ORFs with significant BLASTX hit and UniProt information | 13,380 |

The gene ontology terms for ORFs were extracted wherever possible. The total number GO different terms identified in molecular function biological process and cellular component category are provided in Table 18.

TABLE 18

Gene ontology terms identified in each category

| Category | No of terms |
| --- | --- |
| Biological Processes | 643 |
| Molecular Functions | 849 |
| Cellular components | 234 |

The top 13 terms in each category is mentioned in FIG. 13-15 with three different terms viz. biological processes, molecular functions and cellular components. The organism AGWH #11, total number of Gene ontology have been studied in different categories respectively it is showing 643 in biological processes, 849 in molecular functions and 234 in cellular components.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, in terms of dosage, dilution, application and the different forms of use, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. A herbicidal composition comprising:
   a herbicidal agent obtained from *Setosphaeria monoceras* AGWH#11 as deposited at NCIM and IMTECH under accession number NCIM 1370, MTCC 5974 respectively;
   one of a surfactant and a mineral oil; and
   an antibiotic agent.

2. The herbicidal composition according to claim 1, wherein the herbicidal agent is selected from the group consisting of a hyphal inoculum, a spore inoculum, a conidial inoculum, culture broth, and an at least partially purified culture broth.

3. The herbicidal composition according to claim 1, further comprising a cell free culture broth of *Setosphaeria monoceras* AGWH#11.

4. The herbicidal composition according to claim 1, further comprising a culture medium for *Setosphaeria monoceras*.

5. The herbicidal composition according to claim 1, further comprising a nutrient source for *Setosphaeria monoceras*.

* * * * *